(12) United States Patent
Gammell et al.

(10) Patent No.: US 8,476,244 B2
(45) Date of Patent: Jul. 2, 2013

(54) METHOD OF PRODUCING RECOMBINANT BIOLOGICAL PRODUCTS

(75) Inventors: Patrick Gammell, Dublin (IE); Niall Barron, Dublin (IE); Martin Clynes, Dublin (IE)

(73) Assignee: Dublin City University, Dublin (IE)

( * ) Notice: Subject to any disclaimer, the term of this patent is extended or adjusted under 35 U.S.C. 154(b) by 198 days.

(21) Appl. No.: 12/376,345

(22) PCT Filed: Aug. 3, 2007

(86) PCT No.: PCT/IE2007/000078
§ 371 (c)(1),
(2), (4) Date: Mar. 20, 2009

(87) PCT Pub. No.: WO2008/015662
PCT Pub. Date: Feb. 7, 2008

(65) Prior Publication Data
US 2010/0190258 A1    Jul. 29, 2010

(30) Foreign Application Priority Data
Aug. 4, 2006 (IE) .................................. S2006/0587

(51) Int. Cl.
*C12N 15/11* (2006.01)
(52) U.S. Cl.
USPC ...................................................... 514/44 A
(58) Field of Classification Search
USPC ...................................................... 514/44 A
See application file for complete search history.

(56) References Cited

U.S. PATENT DOCUMENTS
2005/0261218 A1 * 11/2005 Esau et al. ...................... 514/44

FOREIGN PATENT DOCUMENTS
WO    2005/013901 A2    2/2005
WO    2006/027776 A1    3/2006

OTHER PUBLICATIONS

Cheng et al, (2005), "Antisense inhibition of human miRNAs and indications for an involvement of miRNA in cell growth and apoptosis", Nucleic Acid Research, vol. 33(4), pp. 1290-1297.
Bollati-Fogolin et al., (2005), "Temperature reduction in cultures of hGM-CSF-expressing CHO cells: Effect on productivity and product quality", Biotechnology Progress, vol. 21(1): pp. 17-21.
Butler, M., (2005), "Animal cell cultures: recent achievements and perspectives in the production of biopharmaceuticals", vol. 68(3), pp. 283-291.
Gammell, P., (2007), "MicroRNAs: recently discovered key regulators of proliferation and apoptosis in animal cells; Identification of miRNAs regulating growth and survival", Cytotechnology, vol. 53(1-3): pp. 55-63.
Gammell et al., (2007), "Initial identification of low temperature and culture stage induction of miRNA expression in suspension CHO-K1 cells ", Journal of Biotechnology, vol. 130(3): pp. 213-218.
Barron, et al., Engineering CHO cell growth and recombinant protein productivity by overexpression of miR-7, Journal of Biotechnology, vol. 151, Issue 2, Jan. 20, 2011.

* cited by examiner

*Primary Examiner* — Brian Whiteman
(74) *Attorney, Agent, or Firm* — Knobbe Martens Olson & Bear, LLP

(57) ABSTRACT

A method of producing a recombinant biological product, which method employs a mammalian producer cell culture, comprises the steps of generating a biomass of mammalian producer during an initial phase of cell culture, and causing an increase in a level of one or more of the miRNA molecules of Table 1 within the mammalian producer cells once a desired concentration of mammalian producer cells has been achieved. The method may also comprise the step of increasing a level of an inhibitor of one or more of the miRNA molecules of Table 1 within the mammalian producer cells at the start of or during an initial phase of culture.

17 Claims, 4 Drawing Sheets

METHOD OF PRODUCING RECOMBINANT BIOLOGICAL PRODUCTS

This application is U.S. National Phase of International Application PCT/IE2007/000078, filed Aug. 3, 2007 designating the U.S., and published in English as WO 2008/015662 on Feb. 7, 2008, which claims priority to Ireland Patent Application No. S2006/0587, filed Aug. 4, 2006.

REFERENCE TO SEQUENCE LISTING, TABLE, OR COMPUTER PROGRAM LISTING

The present application incorporates by reference the sequence listing submitted as an ASCII text filed via EFS-Web on Jun. 11, 2012. The Sequence Listing is provided as a file entitled 13394567.txt, created on Jun. 4, 2012, which is 6.76 Kb in size.

TECHNICAL FIELD

The invention relates to methods for the generation of Chinese hamster ovary (CHO) cell cultures, and methods of producing recombinant biopharmaceutical products using CHO cell cultures. The invention also relates to recombinant CHO cell lines.

BACKGROUND OF THE INVENTION

Chinese hamster ovary cells (CHO) are the most widely used cell line for the manufacture of recombinant proteins for pharmaceutical use and processes involving CHO variants account for enormous annual revenue (Andersen and Krummen, 2002). Despite the lack of a fully sequenced genome, a number of important CHO transcriptional profiling studies have been carried out either using non-CHO arrays (Baik et al., 2006) or proprietary CHO cDNA arrays (Wong et al., 2006). These studies have described the effects of both low temperature and the induction of apoptosis during CHO culture. Similarly, a number of proteomic studies have investigated the proteome of CHO and the changes in protein expression in response to culture conditions such as temperature (Baik et al.,2006; Champion et al., 1999; Van Dyk et al. 2003; Kaufmann et al., 1999 Lee et al.,2003). These studies have increased overall understanding of the regulation of CHO function and particularly with respect to the effects of reduced temperature.

Low temperature culture of recombinant production CHO cell lines has been shown to result in sustained viability and increased specific productivity (Al-Fageeh et al., 2006; Fogolin et al., 2004; Furukawa and Ohsuye, 1998; Kaufmann et al., 1999) while maintaining the standard of product quality (Fogolin et al., 2005; Yoon et al., 2003b). The most obvious result of lowering the culture temperature is the immediate reduction in growth rate, other effects include lowered metabolism (glucose consumption, oxygen uptake, lactate & ammonium production) and increased resistance to shear and apoptosis (Chuppa et al., 1997; Furukawa and Ohsuye, 1998; Moore et al., 1997; Yoon et al., 2003a). The reduction in growth rate is linked to an accumulation of cells in G1 phase of the cell cycle (Hendrick et al., 2001; Kaufmann et al., 1999; Yoon et al., 2003 a,b) and G1 phase arrest has been linked to the increased productivity (Fussenegger, 2001).

Due to the reasons listed above, many cell culture processes operate a biphasic culture whereby cells are grown at 37° C. to maximise biomass and then the cells are shifted to a lower temperature to encourage protein production while maintaining a longer and more viable stationary/production phase (Fogolin et al.,2004, 2005; Butler, 2005; Fox et al., 2004). Two of the best-known proteins induced following temperature shift are cold inducible RNA binding protein (CRIP) and RMB3. Of these, CRIP is known to cause growth arrest under conditions of low temperature (Danno et al., 2000; Nishiyama et al., 1997, Sonna et al., 2002) however overall, little is known about how mammalian cells respond to reduced temperatures.

miRNAs are small (~22nt) non-coding RNAs (ncRNAs) that regulate gene expression at the level of translation. Each miRNA apparently regulates multiple genes and hundreds of miRNA genes are predicted to be present in mammals (Lim et al. 2003). The first miRNA was discovered in C. elegans in 1993 (Lee et al., 1993) and over the last number of years it has become apparent that there are a huge number of these molecules (up to 2% of the human genome encode miRNAs (Miska, 2005)). Recently miRNAs have been found to be critical for development (Ambros, 2003; Chen et al., 2004), cell proliferation and cell death (Brennecke et al. 2003), apoptosis and fat metabolism (Xu et al. 2003), and cell differentiation (Chang et al. 2004).

STATEMENT OF INVENTION

The present invention is based on a finding that certain miRNA molecules are differentially expressed at different stages of the growth cycle of mammalian producer cells. Accordingly, the invention relates to the modification of mammalian producer cells to increase or decrease levels of specific miRNAs (i.e. as shown in Table 1) in an appropriate temporal manner to modulate growth of the cell culture. In one embodiment, expression of miRNA's is promoted to promote cell arrest. This cell arrest is associated with accumulation of cells in the G1 (growth arrest) phase of the cell cycle and this is linked to increased productivity. In a different, but linked, embodiment, the inhibition or depression of specific miRNAs at the initial phase of culture is promoted, thereby encouraging biomass generation prior to growth arrest. This has the advantage of generating an increased working stock of cells in a shorter time. In one embodiment, inhibition (or repression) of specific miRNAs at the initial phase of culture is initially promoted, and then the conditions are changed to cause an increase in the level of miRNA's during the growth arrest phase of the cell cycle (i.e. through transient transfection with miRNA's, inducing the expression of nucleic acids encoding miRNA's, or through the removal of repressors). These methods find application in the growth and use of mammalian producer cell cultures, particularly in the production of recombinant biological products, especially recombinant biopharmaceutical products.

In this specification, the term "mammalian producer cells" should be understood as meaning mammalian cells useful in the production of recombinant biological products such as biopharmaceuticals and the like. Examples of such cell types would be Chinese hamster ovary (CHO) cells or baby hamster kidney (BHK) cells.

According to the invention, there is provided a method of producing recombinant biological products, which method employs a mammalian producer cell culture, comprising the steps of:
 (a) generating a biomass of mammalian producer cells during an initial phase of cell culture; and
 (b) causing an increase in a level of one or more of the miRNA molecules of Table 1 within the mamamalian producer cells once a desired concentration of mammalian producer cells has been achieved.

A person skilled in the art would know when a desired concentration of mammalian producer cells is achieved. Generally, this would be at, or just prior to, the start of the growth arrest phase of the cell cycle.

Typically, the cells are transiently transfected with one or more of the miRNA molecules of Table 1. Suitably, the miRNA molecules are miRNA precursor molecules, ideally synthetic miRNA precursor molecules. However, the miRNA molecules may be primary miRNA or mature miRNA molecules. The sequences of the primary, precursor and mature miRNA's molecules of Table 1 is available from the database of miRNA sequences, targets and gene nomenclature, MIRBase, at http:microrna.sanger.ac.uk Alternatively, the cells may be transiently transfected with an expression vector comprising a nucleic acid sequence coding for a miRNA molecule of Table 1 under the control of a transcriptional promoter. Typically, the nucleic acid sequence codes for a precursor of a miRNA molecule of Table 1. Suitably, the transcriptional promoter is a constitutive or inducible promoter. Ideally, the promoter is temperature inducible, and is ideally switched on in biphasic cell cultures when the temperature drops. With this method of transient transfection using an expression vector, the nucleic acid sequence may also code for a primary miRNA or a mature miRNA, however generally the vector codes for the precursor version of any of the miRNA molecules of Table 1. The expression vector may be a plasmid, or a linear nucleic acid construct such as a PCR product or a restriction fragment.

In one embodiment of the invention, the transfection is mediated using a liposome-based method such as, for example, NeoFx (Ambion Cat:4511). However, other methods of transfection will be apparent to the skilled person such as, for example, transfection mediated using electroportation or transfection mediated using calcium phosphate.

As an alternative to transient transfection, the method may employ cells that are engineered to have the coding sequence for a miRNA molecule of Table 1 stably integrated into the cell genome under the control of an inducible promoter, and in such cases the method generally involves inducing the expression of the miRNA molecule at a desired point in the growth cycle, generally at or just prior to the start of the cell arrest phase (i.e. when a desired concentration of viable producer cells have been achieved). Typically, the promoter is a temperature inducible promoter, In such circumstances, the temperature drop from 37° to 31° will induce expression of the miRNA molecules. The coding sequence for the miRNA molecule may code for primary, precursor, or a mature version of the miRNA; generally it will code for the precursor version of the miRNA molecule, and the precursor will be processed into mature miRNA by the machinery of the cell.

In one embodiment of the invention, miRNA coding sequences in the cells are repressed using suitable repressors during an initial phase of growth, and then the level of miRNA in the cells is increased by withdrawal of the repressor at or just prior to the growth arrest phase. Suitable promoter/repressor pairs will be well known to those skilled in the art.

In a preferred embodiment of the invention, the miRNA molecule is selected from the group comprising: hsa-miR-21; and hsa-miR-24.

In another aspect, the invention also provides a method of producing recombinant biological products, which method employs a mammalian producer cell culture, the method comprising the step of increasing a level of an inhibitor of one or more of miRNA molecules of Table 1 within the cells during an initial phase of culture, and typically at the start of the initial phase of culture. The sequences of such inhibitors are available from the database of miRNA sequences, targets and gene nomenclature, MIRBase, at http:microrna.sanger.ac.uk Suitably, the method employs cells that are engineered to have the coding sequence for a miRNA inhibitor molecule stably integrated into the cell genome under the control of an inducible promotor, and wherein the method involves inducing the expression of the miRNA inhibitor molecule during the initial phase of culture, and ideally at the start of the initial phase of culture. This has the effect of encouraging biomass generation prior to growth arrest, which has the advantage of generating an increased working stock of cells in a shorter time Suitably, expression is induced by the presence of an inducer of expression. Alternatively, the sequence coding for the inhibitor may be under the control of a repressible promoter. In this case, the inhibitor will be freely expressed during the initial phase of culture, with a repressor being added to inhibit expression of the miRNA inhibitor(s) at a desired stage of the cell cycle, generally at or just prior to the start of growth arrest stage of the cell cycle.

Preferably, the inducing of the expression of the miRNA inhibitor molecule is stopped once a suitable cell biomass is achieved.

In a preferred embodiment, the miRNA inhibitor molecule is selected from the group comprising inhibitors of the following: hsa-miR-21; and hsa-miR-24.

In one embodiment, the invention relates to a method of generating mammalian producer cell culture comprising the step of causing an increase in a level of an inhibitor of one or more of the miRNA molecules of Table 1 within the cells during or at the start of an initial phase of culture according to the invention, and subsequently increasing a level of one or more of the miRNA molecules of Table 1 within the cells at or just prior to a start of the growth arrest phase of the cell cycle according to the invention.

Typically, the methods of the invention are suitable for application in the growth and use of CHO cells such as CHO-K1 or CHO-DUKX cells or BHK cells.

In one embodiment of the methods of the invention, the growth arrest phase is carried out at a lower culture temperature than the initial growth phase. Typically, the initial growth phase is carried out at 37° C. Suitably, the growth arrest phase is carried out at 31° C.

The invention also relates to a mammalian producer cell comprising a nucleic acid encoding a miRNA molecule of Table 1 stably incorporated into the genome of the cell and under the control of an inducible promoter. Preferably, the nucleic acid encodes a miRNA molecule selected from the group comprising: hsa-miR-21; and hsa-miR-24. Suitably, the promoter is a temperature inducible promoter.

Alternatively, or in addition, the mammalian producer cell of the invention may comprise a nucleic acid encoding an inhibitor of a miRNA molecule of Table 1, stably incorporated into the genome of the cell and under the control of an inducible promoter. Suitably, the nucleic acid encodes an inhibitor of an miRNA molecule selected from the group comprising: hsa-miR-21; and hsa-miR-24. Suitably, the promoter is a temperature inducible promoter.

Typically, the mammalian producer cell is a CHO cell such as, for example, a CHO-K1 cell or a CHO-DUKX cell. Alternatively, the mammalian producer cell may be a BHK cell. These cells may be obtained from LGCProtochem-atcc of Middlesex, England under the following catalogue references: CRL-10154-CHO DuKX; CRL-9618-CHOK1; CCL-10-BHK-21.

Thus, the mammalian producer cell lines of the invention may be genetically engineered to inducibly express specific miRNA molecules (of Table 1) at or just before the growth arrest phase to generate an increased level of the miRNA molecules during the growth arrest phase, or they may be engineered to inducibly express inhibitors of the miRNA molecules of Table 1 during the initial stages of the cell culture, or they may be engineered to do both, i.e. express inhibitors of the miRNA molecules during the initial stages of the culture, and then express the miRNA molecules during cell arrest phase.

It will be appreciated that in the methods and cell lines of the invention, that control of expression may exercised by using inducible promotors and then adding or removing the inducers to the culture broth as required. The skilled person will appreciate that the methods and products of the invention may also be controlled by using constitutive promotors and controlling expression by the use of repressors of expression. Thus, in this specification, where the term "inducible promoter" is used, it should be appreciated that constitutive promotors may be used as an alternative, and that the modification of the methods or of the mammalian producer cell lines that is required to achieve the promise of the invention will be apparent to the skilled person.

The invention also provides a kit useful for producing recombinant biological products, the kit comprising: (a) a mammalian producer cell line; (b) means for transfecting the cells with a miRNA molecule of Table 1; and/or (c) means for transfecting the cells with an inhibitor of one of the miRNA molecules of Table 1. The transfection means may be transient or stable, and involves introducing into the cells either or both of (a) synthetic miRNA molecules (or inhibitors) and (b) nucleic acid encoding miRNA molecule (or encoding the miRNA inhibitors).

DETAILED DESCRIPTION OF THE INVENTION

Figure 1:
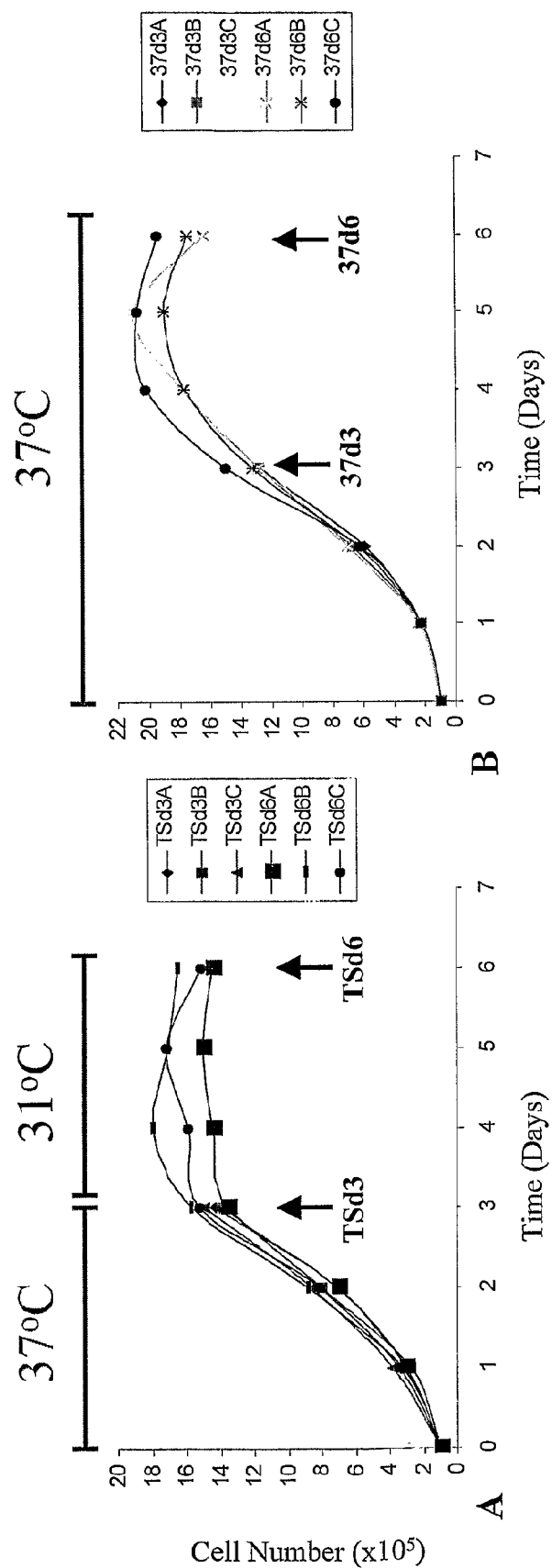
FIG. 1. Viable cell counts for CHO-K1 batch culture following seeding at $1 \times 10^5$ cells/ml for cultures incorporating a temperature shift (A) and cells cultured at a constant temperature of 37° C. In each case biological triplicate samples were taken from the spinner flasks at 72 and 144 hours post seeding (indicated by arrows).

Materials and Methods
Cell Line and Cell Culture
Suspension adapted CHO-K1 cells were used in this study. The culture medium consisted of ATCC medium (DMEM/F-12 Hams containing glutamine and sodium pyruvate; Sigma) supplemented with 10% fetal bovine serum (Sigma). Cells were maintained in 250 mL spinner vessels (Techne) at 60 rpm on spinner platforms in 37° C. or 31° C. incubators as appropriate. For batch culture experiments, exponentially growing cells were inoculated at $1 \times 10^5$ cells/mL into spinners vessels at a final volume of 100 mL. All cultures were gassed with compressed air (Air Products) each day for ~1 min. Cell counts were taken every 24 hours, cell concentration was determined using a hemacytometer and viable cells were distinguished from dead cells using the tryphan blue exclusion method. For both temperature shift and continuous batch culture at 37° C., triplicate spinner vessels were sacrificed for sampling at 72 and 144 hours.

RNA Sampling and Extraction
Upon sampling, cell pellets were washed twice in PBS and lysed using the lysis/binding solution provided in the MiRVana extraction kit (Ambion). These lysates were stored at ~80° C. until required for extraction. Extraction via organic and column based methods were as outlined by the manufacturers instructions. RNA quality was determined by using both Agilent 6000 nano chips and by 15% denaturing acrylamide gel electrophoresis. RNA quantification was carried out using a Nanodrop (ND-1000; Labtech. International).

MiRNA Bioarray Analysis.
Samples for microRNA profiling studies were processed by Asuragen according to the company's standard operating procedures. The microRNA enriched fraction was obtained by passing 10 μg of total RNA through a flashPAGE™ Fractionator apparatus (Ambion, Inc., Austin, Tex.) and cleaned and concentrated using the flashPAGE Reaction Clean-Up Kit (Ambion, Inc., Austin, Tex.). The 3' ends of the RNA molecules were tailed and labeled using the mirVana™ miRNA Labeling Kit (Ambion, Inc., Austin, Tex.) according to the manufacturer's instructions. Amine-modified nucleotides were incorporated during the poly (A) polymerase mediated tailing reaction, and Cy5 succinimide esters (Amersham Biosciences (GE Healthcare), Piscataway, N.J.) were conjugated to the amine moieties on the microRNAs. Hybridization to the mirVana miRNA Bioarrays (Ambion, Inc., Austin, Tex.) was performed using the mirVana miRNA Bioarray Essentials Kit (Ambion, Inc., Austin, Tex.). The Cy5 fluorescence on the arrays was scanned at an excitation wavelength of 635 nm using a GenePix 4200AL scanner (Molecular Devices, Union City, Calif.). The fluorescent signal associated with the probes and local background was extracted using GenePix Pro (version 6.0, Molecular Devices, Union City, Calif.).

Thresholding and signal scaling were generated using algorithms selected by Asuragen, as implemented as part of the microRNA Standard Service Premium Analysis (miSSP package). The background adjusted fluorescent values generated by GenePix Pro were normalized for each microRNA using a variation stabilization transformation method described by Huber et al., 2002. Hypothesis testing with one-way ANOVA or t-Test depending on the number of groupings in the experimental design For Multiple Group comparisons, we use the One-way ANOVA (Analysis Of Variance) model to test the null hypothesis, which states there is no difference between groups. The goal is to filter out genes that have the same expression level across all groups.

Pair-wise comparisons are carried out on differentially expressed genes identified by ANOVA to see how they differ from each other. For each pair of treatments, a two-sample t-test is carried out for every gene and multiplicity correction is followed to control the false discovery rate (FDR) using a step-up approach as described by Benjamini and Hochberg (1995) using an FDR of 5%. This method is referred to as "protected Least Significant Difference (LSD)". The detailed miRNA lists and associated information such as fold-change and p-values are reported.

MiRNA profiling of temperature shifted CHO-K1 cells at 144 hours of culture vs. exponentially growing CHO-K1 cells at 37° C. identified 26 miRNAs as being significantly different (Table 1).

TABLE 1

| MiRNA ID | SEQUENCE ID NO |
|---|---|
| hsa_miR_30d_MM1 | 1 |
| hsa_miR_191 | 2 |
| hsa_miR_495 | 3 |
| hsa_miR_320 | 4 |
| hsa_miR_10a | 5 |
| hsa_miR_126_AS | 6 |
| hsa_miR_30c | 7 |
| hsa_miR_181a | 8 |
| hsa_miR_21 | 9 |
| hsa_miR_30d | 10 |
| hsa_miR_29a | 11 |
| hsa_miR_125b | 12 |
| hsa_miR_513 | 13 |
| hsa_miR_107 | 14 |
| hsa_miR_27a | 15 |
| hsa_miR_449 | 16 |
| mmu_miR_298 | 17 |
| hsa_miR_24 | 18 |
| hsa_miR_221 | 19 |
| hsa_miR_516_3p | 20 |
| mmu_miR_7b_MM1 | 21 |
| hsa_miR_197 | 22 |
| hsa_miR_19b | 23 |
| mmu_miR_346 | 24 |
| hsa_miR_10b | 25 |
| Has_let_7f | 26 |

The sequences of the mature transcripts the above miRNA's are provided in the Sequence Listing below. The sequence of the primary and precursor transcripts of the above miRNA's may be obtained from the database of miRNA sequences, targets and gene nomenclature, MIRBase, at http:microrna.sanger.ac.uk The content and use of the database is explained in the Griffiths-Jones et al. article.

The miRNA inhibitor sequences employed in the methods of the invention are exact antisense sequences of the mature miRNAs of Table 1, available from the Sanger miRNA repository (now the miRBase database operated by the University of Manchester, United Kingdom). The inhibitors are modified to have 2' Ome modifications and a 3' C3 containing amino linker (Angie M. Cheng, Mike W. Byrom, Jeffrey Shelton and Lance P. Ford* "Antisense inhibition of human miRNAs and indications for an involvement of miRNA in cell growth and apoptosis" Nucleic Acids Research 2005 33(4): 1290-1297.)

Inhibitors of the miR-21 and miR-24 miRNA's are commercially available form Ambion under catalogue references AM10206 (miR-21) and AM10737 (miR-24).

For the detection and quantification of specific miRNAs the miRVana qRT-PCR miRNA detection kits and primer sets were used according to manufacturers instructions. In all cases SuperTaq (Ambion) was used for polymerisation reactions. Detection and normalisation was facilitated using SYBR green and ROX normalisation dyes (Invitrogen). Both RT and PCR reactions were carried out using an ABI 7500 Real-Time PCR System (Applied Biosystems, Foster City, Calif.). Biological replicate results were checked for statistical significance using a students t-test with a p value cut-off of 0.05.

Primers were designed for cloning *Cricetulus griseus* miR-21 based on alignment of the corresponding genomic regions flanking the pre-miR-21 sequence from *Mus musculus, Rattus norvigicus* and *Homo sapiens*. The primers used were 5' atgtttgctttgctttaaaccctgcctgagca3' and 5' ctgcaaaccatgatgctgggtaatgtttga3'. Genomic DNA was extracted from approx. 5×10$^6$ CHO-K1 cells (Whole blood extraction kit, Nucleon) and eluted in 100 ul water. 1.5 ul (~100 ng) DNA was used as template for PCR. The reaction also contained 400 nM of each primer, 1 ul DMSO and 20.5 ul Platinum Supermix (Invitrogen). Cycling conditions were: 3 min at 95° C., 30 cycles of 30 sec at 94° C., 30 sec at 53° C. and 45 sec at 72° C., followed by 7 mins at 72° C. PCR product was checked on an agarose gel for a specific band of appropriate length (ca.220 bp) and the remainder of the mix cleaned up (Qiagen PCR cleanup kit) for sequencing. Sequencing was performed on both strands using the cloning primers (MWG Biotech, Germany).

Results

Cell Culture

Suspension adapted CHO-K1 cells were seeded at 1×10$^5$ cells/ml in spinner flasks (supplier) and cultured for either 37° C. for 6 days or for 3 days at 37° C. followed by a temperature shift to 31° C. for a further 3 days. As can be seen in FIG. 1 the cells that were temperature shifted immediately ceased logarithmic growth and did not exceed a peak viable cell density of 1.67×10$^6$±0.15 cells/ml whereas the cells cultured at 37° C. continued in logarithmic growth for a further 24 hours and achieved average peak viable densities of 2.02×10$^6$±0.11 cells/ml. Cells were sampled at 72 hours and 144 hours for RNA and protein extraction. The cell pellets were washed twice in PBS and immediately lysed in miRVana lysis/binding buffer and stored at −80° C. until extraction using Ambion's mirVana miRNA isolation kit.

Figure 2:
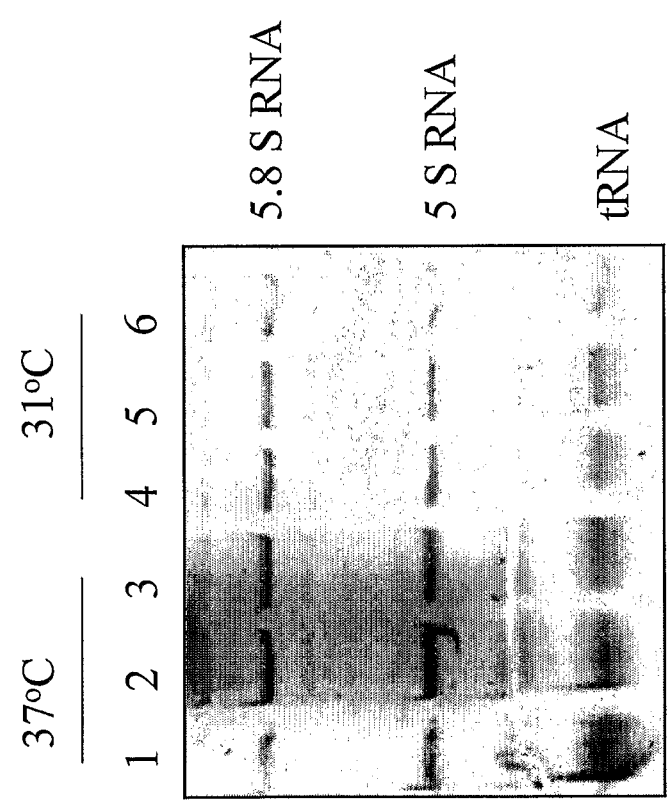
FIG. 2. 15% denaturing acrylamide gel analysis of RNA extracted from the TS samples demonstrating the yield and integrity of the small RNA species.

Total RNA was QC'd using both an Agilent Bioanalyzer and the presence and integrity of small RNA species was confirmed by visualisation on a 15% denaturing polyacrylamide Gel (FIG. 2).

miRNA Bioarray Analysis.

Biological triplicate samples of total RNA isolated at day 3 (TSd3) and day 6 (TSd6) were extracted from the cells that were shifted to 31° C. at 72 hours and subsequently used for miRNA bioarray analysis.

Figure 3:
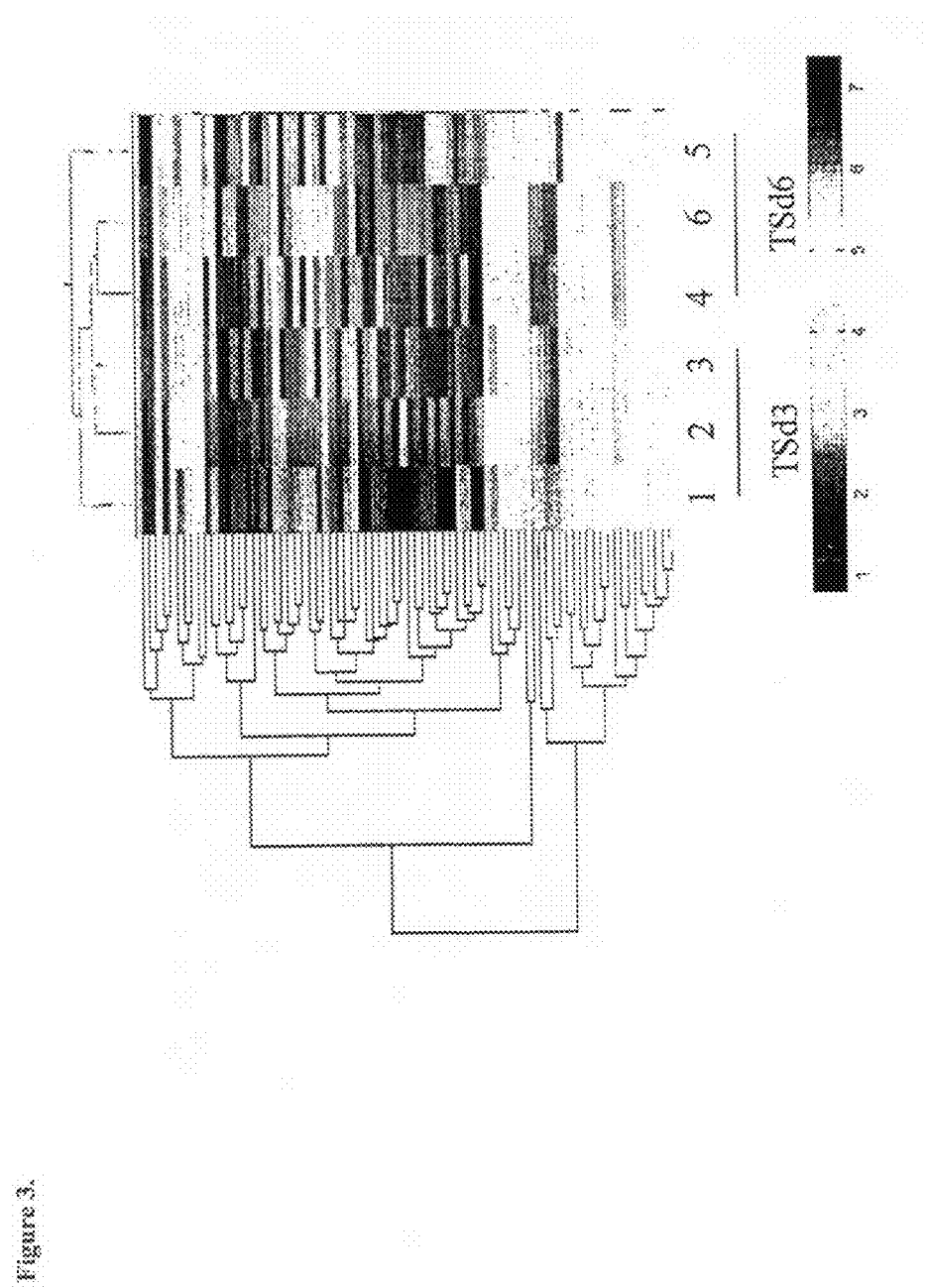
FIG. 3. Unsupervised clustering analysis of all 6 CHO-K1 samples results in 2 main clusters of samples which separate the exponential (37° C.) samples from the quiescent (31° C.) samples. From the cluster tree structure at the top it is clear to see that samples 1 (TSd3A) and sample 5 (TSd6B) are outliers. The relative expression of each miRNA is represented by colour ranging from low (Blue) to high (Red) expression. The range bar of relative expression is given below the cluster.

When miRNA bioarrays were probed with labelled *Cricetus griseus* RNA, the average percent present call was in the region of 27.3% (±4.8), this compares favourably with human cell line RNA which had an average present call of 26.9% (±5.7). The average flourescence signal from arrays probed with CHO-K1 RNA was 306.4±55.2 Fluorescence Units which was comparable to the human cell data (296.6±71.5). Unsupervised cluster analysis of the expression data revealed that CHO-K1 samples clustered as a discrete sub-cluster separate to six human cell lines included in the analysis as non-hamster controls (data not shown). Unsupervised clustering within the CHO-K1 samples resulted in separation of the exponential 37° C. samples from those at stationary phase grown at 31° C. (FIG. 3). Within the sub clusters it is clear that spinner samples 1 (TSd3A) & 5 (TSd6B) are outliers and it is likely an artefact of labelling and/or hybridisation due to overall lower median foreground readings and lower percent present calls associated with these arrays. This is an important quality control metric for subsequent analysis steps.

Figure 4:
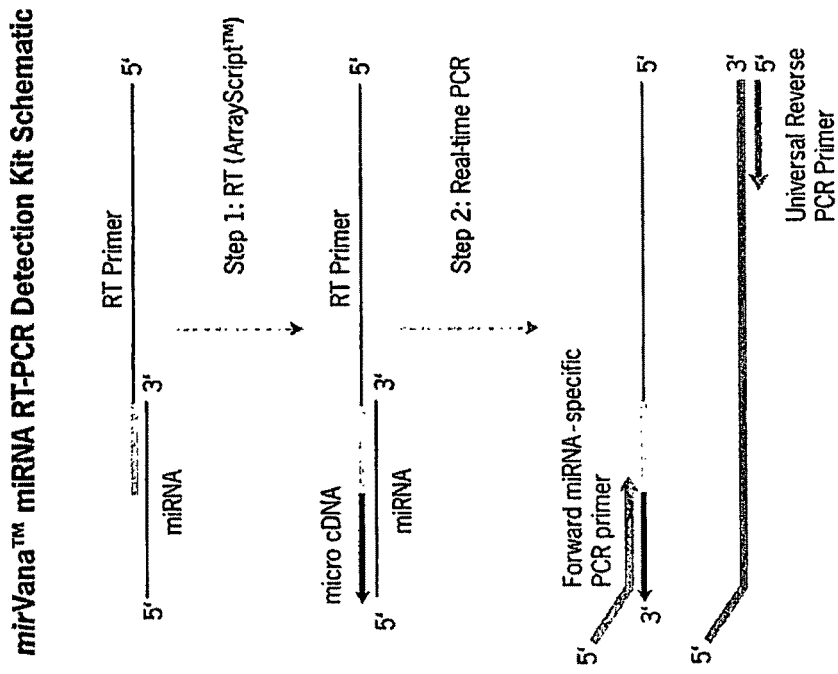
FIG. 4. An outline of the Ambion qRT-PCR process for the detection and quantification of mature miRNAs. This image has been used courtesy of Ambion Inc.

Using the statistical methods outlined in the materials and methods to analyse all samples it was found that 26 miRNAs were considered statistically different (p≦0.05) between the 72 hour (TSd3) and 144 hour (TSd6) samples (Table I Quantitative QRT-PCR Analysis of specific miRNA expression in CHO-K1 Total RNA from CHO-K1 cells cultured at 37° C. for 144 hours was sampled at day 3 (37d3), and day 6 (37d6) (FIG. 1b) and RNA from cells incorporating a temperature shift at day 3 (TSd3 & TSd6) was used for the qRT-PCR analysis of selected targets from the bioarray analysis. Initial experiments indicated that optimal results could be achieved using 2.5 ng of RNA per reaction and in the case of the 5S endogenous control to use 1/10 dilution of the PCR-primer. 5S RNA was shown to be expressed at similar levels in all samples regardless of growth phase or culture temperature, which is consistent with the quality control analysis in FIG. 2. The principle of the qRT-PCR reaction for miRNAs employs a proprietary RT-primer specific for the 3' end of a specific miRNA which is then extended to a micro-cDNA by an ArrayScript™ enzyme during the RT-reaction step. The qPCR step is carried out in-situ and uses a 5' miRNA specific primer and a 3' universal primer targeting universal 3' end of the original RT-primer (FIG. 4). Hence this is a highly specific means of amplifying individual mature miRNAs.

To ensure that the miRNAs detected using the bioarray and q-RT-PCR were in fact true hamster orthologues of the human and mouse miRNAs on the bioarray, a representative miRNA was selected (miR-21) for cloning and sequencing. As can be seen in Table 2 below, the mature miR-21 is conserved across all species for which sequence is available but the entire precursor sequence is completely identical to that of Rat.

activity, shear sensitivity and apoptosis rates observed following temperature shift have encouraged its use in recombinant protein production (Fogolin et al., 2004; Fogolin et al., 2005; Fox et al., 2004).

MiRNA profiling of temperature shifted CHO-K1 cells at 144 hours of culture vs. exponentially growing CHO-K1 cells at 37° C. identified 26 miRNAs as being significantly different (Table 1). Overall profiling analysis of CHO-K1 RNA clearly demonstrated that Ambion bioarrays are suitable for CHO profiling based on percent present calls and median spot intensities. When the CHO-K1 profiles were compared to 6 human cell lines, it was clearly observed that CHO-K1 are uniquely different in the profile of miRNAs they express. qRT-PCR validation studies showd that miR-21 and miR-24 were found to be significantly upregulated in CHO-K1 cells at the end of the batch run in a non-temperature dependent manner. The relative expression levels of the individual miRNAs identified on the bioarray were reflected by the qRT-PCR data, indicating a quantitative as well as qualitative aspect to the bioarray.

The association of miR-21 and miR-24 with growth inhibition is in keeping with the results observed here in that both miRNAs are elevated in quiescent cells and it is possible that in this system miR-21 is not a significant factor in regulating apoptosis. Preliminary analysis in this laboratory has indicated that miR-21 levels are elevated in cells continuously cultured at 31° C. and again this is associated with slow growth.

TABLE 2

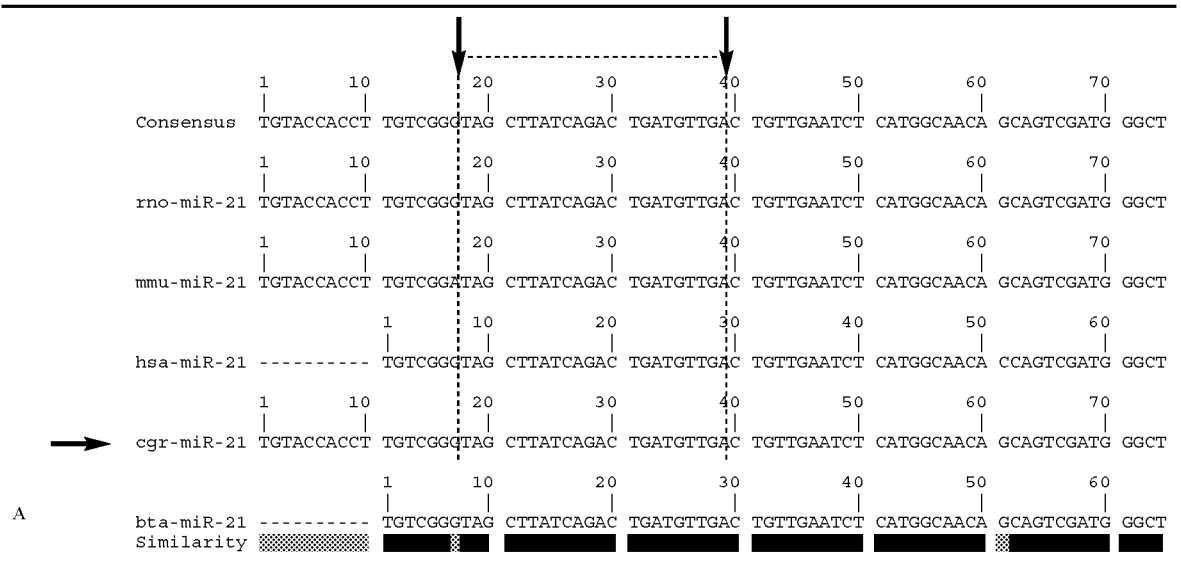

A. Alignment of CHO-K1 cgr-miR-21 sequence with the sequences of mouse (mmu-), rat (rno-), human (hsa-) and bovine (bta-) miR-21. The CHO sequence is identical to that of rno-miR-21 published in the Sanger miRNA repository (now the miRBase database operated by the University of Manchester, United Kingdom).
The consensus sequence and sequences of rno-miR-21, mmu-miR-21, has-miR-21, cgr-miR-21, and bta-miR-21 are provided as SEQ ID NOs. 27-32, respectively in the Sequence Listing.
B. Predicted stem loop structure of cgr-miR-21 with the mature miRNA highlighted in red. The aligned sequences are provided as SEQ ID NOs: 33 and 34 in the Sequence Listing.

Discussion

As shown in FIG. 1 reducing the culture temperature has an immediate effect on cell growth and it can be seen also that after 144 hours of culture, the cells at 31° C. maintain a steady viable cell number whereas the cells cultured at 37° C. are entering late stationary/death phase. The reduced metabolic In the examples above above, the Applicant has identified increased expression of a number of miRNAs in Chinese hamster ovary cells (CHO) upon cessation of proliferation either due to reduced temperature culture or through normal stationary phase growth resulting from nutrient limitation and waste product accumulation. The identification that the mature miR-21 is completely conserved throughout the mammalian species checked confirms the theory that mature miRNAs are largely conserved amongst mammalian cell lines. This enables modification of CHO cells to overexpress specific miRNAs using artificial mammalian (e.g. murine or human) miRNA precursor molecules (commercially available from Ambion Cat:17100) or to inhibit miRNA action using specific miRNA inhibitor molecules (commercially available Ambion Cat:17000). As the efficient production of biopharmaceuticals generally employs biphasic cultures having an initial growth phase at 37° C. to generate sufficient biomass followed by a production phase at a lower culture temperature, the Applicant proposes that the miRNA molecules of Table 1, and/or inhibitors of the miRNA molecules, may be employed to create the conditions, or augment existing conditions, necessary for the efficient growth and use of CHO cell culture, especially in the production of recombinant biopharmaceutical products.

Case 1: Transient Transfection of miRNAs to Inhibit CHO Growth

CHO cell behaviour in culture is modified using synthetic miRNA precursor molecules miR-21 (Table 1) (Ambion Cat: 17100) which is introduced into CHO-K1 cells (LGSProtochem-atcc catalogue ref: CRL-9618-CHOK1) once sufficient biomass is achieved (usually at achieving about 80% of maximal viable cell density). The purpose of this transfection is to inhibit growth without necessitating temperature shift and/or to enhance the beneficial effects of reducing culture temperature by transiently transfecting the specific miRNAs in Table I (alone or in combination) at the same time. The transfection is mediated via conventional liposome based methods including NeoFx (Ambion Cat:4511). The methods used are according to manufacturers instructions.

Case 2. Transient Expression of miRNA Coding Sequences to Inhibit CHO Growth.

CHO behaviour in culture is modified using synthetic miRNA coding sequences in expression vectors (Ambion Cat: 5775, 5777, 5779) (or linear expression molecules obtained from a PCR reaction or as a restriction fragment) which are introduced into cells once sufficient biomass is achieved. (Usually at about 80% of maximum achievable viable cell density) These expression constructs contain at least the following components—a transcription promoter (constitutive or inducible, of viral, mammalian or other origin) and a sequence coding for an miRNA precursor molecule. The pSILENCER expression cassette employed conatins a modified RNA pol II type CMV promoter and optimised SV40 polyadenylation signals to drive high level expression. This facilitates high expression in a broad range of cells. The purpose of this transfection is to inhibit growth without necessitating temperature shift and/or to enhance the beneficial effects of reducing culture temperature by transfecting the specific miRNAs in Table I (alone or in combination) at the same time. The transfection is mediated via conventional liposome based methods including Lipofectamine 2000 (Invirogen). The methods used are according to manufacturers instructions.

Case 3. Stable Expression of miRNA Coding Sequences to Inhibit CHO Growth.

Novel CHO based cell lines are generated which have the coding sequences for the miR-21 or miR-24 miRNAs of Table I stably integrated in the cell genome under the control of the inducible promoter, MT. This promoter is inactive until specific signals are received to activate the promoter (i.e. $ZnSO_4$)—once these signals are received then any coding sequences under the control of the promoter are transcribed.

The method involves subcloning the miRNA coding sequence from the commercially available expression systems (Ambion Cat: 5775, 5777, 5779) into an inducible system e.g. pCytTS (Cytos biotechnology). Other possible expression systems are complete control® system (Stratagene) or pSUPERIOR (Oligoengine) (this may also be achieved by modifying the Ambion vectors to include inducible promoters). These new expression systems are transfected into CHO cells using conventional liposome based transfection agents such as Lipofectamine 2000 (Invitrogen) according to manufacturers instructions. Following isolation of homogenous clonal populations using selection with an appropriate selective agent, the new cell lines are grown normally in exponential growth until the culture temperature is reduced. In the present case, the expression of the miRNA is induced by addition of $ZnSO_4$ at a level of 100 μM. Alternatively, in the case of a temperature inducible promoter the temperature shift alone will result in enhanced growth arrest due to increased expression of growth inhibitory miRNAs (Table 1). Generally, in the case of other inducible promoters, the promoter will be activated by addition or withdrawl of stimulatory/repressor molecules (e.g. tetracycline) to the culture broth. These new cell lines will then be ideally available for further modification to express recombinant glycoproteins for therapeutic purposes.

Case 4. Stable Expression of miRNA Coding Sequences to Promote CHO Growth.

Novel CHO based cell lines are created which have the inhibitor sequences targeting the miRNAs listed in Table 1 under the control of either a temperature inducible promoter or another variety of inducible promoter. The methods will involve subcloning the miRNA inhibitor coding sequence from the commercially available expression systems (Ambion Cat: 5775, 5777, 5779) into an inducible system e.g. complete control® system (Stratagene) or pSUPERIOR (Oligoengine). (this may also be achieved by modifying the Ambion vectors to include inducible promoters). These new expression systems will be transfected into CHO cells using conventional liposome based transfection agents such as Lipofectamine 2000 (Invitrogen). Following isolation of homogenous clonal populations using appropriate selective agents, the new cell lines will grow at accelerated rates during exponential growth at 37° C. in the presence/absence of the inducer/repressor (e.g. tetracycline) until the culture temperature is reduced and the inducer is withdrawn/repressor is added. At this point the expression of the inhibitors will cease. Once the inhibitors are withdrawn this will allow expression of the specific miRNAs, growth inhibition and hence improved production. This system is designed to increase productivity by allowing increased biomass production at the early phases of the culture and then facilitate stationary phase production in a normal fashion. These new cell lines will then be ideally available for further modification to express recombinant glycoproteins for therapeutic purposes.

Case 5 Research Tool.

The stable cell lines generated under Cases 3&4 above are of major interest to industrial researchers through the identification of target molecules and pathways that are affected by the specific miRNA expression/inhibition. MiRNAs act by preventing translation of specific proteins hence methods such as 2D gel electrophoresis can be uses to identify differentially expressed proteins following expression or inhibition of specific proteins and therefore the targets. This has the potential to facilitate rational design approaches to cell line engineering and to process design e.g. the inclusion of specific inhibitor molecules in medium formulations.

The invention is not limited to the embodiments hereinbefore described which may be varied in construction and detail without departing from the spirit of the invention. In this regard, while the main statements of invention relate to methods of producing recombinant biological products, the methods may be likewise employed in methods of generating mammalian producer cell cultures.

The invention claimed is:

1. A method of producing a recombinant biological product comprising:
   (a) generating a biomass of Chinese Hamster Ovary (CHO) cells that produce said recombinant biological product at the start of or during an initial phase of cell culture;
   (b) causing an increase or decrease in a level of one or more miRNA molecules comprising a sequence selected from the group consisting of SEQ ID. NOs.: 9, 18, 21, and orthologous sequences thereof within the CHO cells, wherein said causing an increase comprises (i) transiently transfecting one or more of the miRNA molecules or precursors thereof within the CHO cells, (ii) transiently transfecting an expression vector comprising a nucleic acid sequence coding for one or more miRNA molecules or precursors thereof within the CHO cells, or (iii) stably transfecting a nucleic acid sequence coding for one or more miRNA molecules or precursors thereof into the CHO cell genome, and wherein said causing a decrease comprises increasing a level of an inhibitor of one or more the miRNA molecules;
   (c) reducing, arresting or increasing growth of the culture as a result of the increase or decrease in the level of the one or more miRNA molecules; and
   (d) producing the biological product from the culture.

2. The method as claimed in claim 1 in which the one or more of the miRNA molecules comprise synthetic miRNA precursor molecules.

3. The method as claimed in claim 1 in which the cells are transiently transfected with the expression vector comprising the nucleic acid sequence coding for the one or more miRNA molecules or precursors thereof under the control of a transcriptional promoter.

4. The method as claimed in claim 3 in which the transcriptional promoter is a constitutive or inducible promoter.

5. The method as claimed in claim 1 which employs the CHO cells that are engineered to have the coding sequence for the one or more miRNA molecules or precursors thereof, stably integrated into the cell genome under the control of an inducible promoter, and wherein the method involves inducing the expression of the one or more miRNA molecules or precursors thereof at or just prior to the start of the growth arrest phase of the cell cycle.

6. The method as claimed in claim 5 in which the promoter is a temperature inducible promoter.

7. The method as claimed in claim 1 in which the one or more miRNA molecules is selected from the group consisting of: hsa-miR-21 (SEQ ID NO: 9); and hsa-miR-24 (SEQ ID NO: 18).

8. The method as claimed in claim 1 comprising the step of increasing a level of an inhibitor of one or more the miRNA molecules within the Chinese Hamster Ovary (CHO) cells at the start of or during an initial phase of culture.

9. The method as claimed in claim 1 in which the at least one miRNA is a primary, precursor, or mature form of the miRNA.

10. The method as claimed in claim 8 which employs Chinese Hamster Ovary (CHO) cells that are engineered to have the coding sequence for the inhibitor stably integrated into the cell genome under the control of an inducible promotor, and wherein the method involves inducing the expression of the inhibitor molecule at the start of or during the initial phase of culture.

11. The method as claimed in claim 10 in which expression of the miRNA inhibitor molecule is induced by the presence of an inducer of expression or by the absence of a repressor of expression.

12. The method as claimed in claim 10 in which the inducing of the expression of the miRNA inhibitor molecule is stopped once a suitable cell biomass is achieved.

13. The method as claimed in claim 1, comprising the step of increasing a level of an inhibitor of one or more the miRNA molecules within the Chinese Hamster Ovary (CHO) cells at the start of or during an initial phase of culture, and subsequently increasing a level of one or more of the miRNA molecules within the Chinese Hamster Ovary (CHO) cells prior to or during a growth arrest phase of the cell cycle.

14. The method as claimed in claim 1 in which a growth arrest phase of the growth cycle is carried out at a lower culture temperature than the initial growth phase of the growth cycle.

15. The method as claimed in claim 1, wherein the precursors comprise a precursor of a miRNA consisting of a sequence selected from the group consisting of SEQ ID. NOs.: 9, 18, and 21.

16. The method as claimed in claim 1 in which the one or more miRNA molecule comprises the sequence of SEQ ID NO: 9.

17. A method of producing a recombinant biological product comprising:
   (a) generating a biomass of Chinese Hamster Ovary (CHO) cells that produce said recombinant biological product at the start of or during an initial phase of cell culture;
   (b) causing one or both of steps (b1) and (b2); and
      (b1) causing a decrease in a level of an miRNA molecule comprising a sequence selected from the group consisting of SEQ ID NO: 21 and an orthologous sequence thereof within the CHO cells at an initial stage of cell culture, thereby increasing growth of the cell culture as a result of the decrease in the level of the miRNA molecule; and
      (b2) causing an increase in a level of an miRNA molecule comprising a sequence selected from the group consisting of SEQ ID NO: 21 and an orthologous sequence thereof within the CHO cells at a growth arrest phase, thereby reducing or arresting growth of the culture as a result of the increase in the level of the miRNA molecule,
   wherein said causing a decrease comprises increasing a level of an inhibitor of the miRNA molecule, and
   wherein said causing an increase comprises (i) transiently transfecting the miRNA molecule or a precursor thereof within the CHO cells, (ii) transiently transfecting an expression vector comprising a nucleic acid sequence coding for the miRNA molecule or a precursor thereof within the CHO cells, or (iii) stably transfecting a nucleic acid sequence coding for the miRNA molecule or a precursor thereof into the CHO cell genome, and;
   (c) producing the biological product from the culture.

* * * * *

SEQUENCE LISTING

<160> NUMBER OF SEQ ID NOS: 34

<210> SEQ ID NO 1
<211> LENGTH: 22
<212> TYPE: RNA
<213> ORGANISM: Homo sapiens
<220> FEATURE:
<221> NAME/KEY: miRNA
<222> LOCATION: (1)..(22)

<400> SEQUENCE: 1
uguaaacauc cccgacugga ag                                           22

<210> SEQ ID NO 2
<211> LENGTH: 23
<212> TYPE: RNA
<213> ORGANISM: Homo sapiens
<220> FEATURE:
<221> NAME/KEY: miRNA
<222> LOCATION: (1)..(23)

<400> SEQUENCE: 2
caacggaauc ccaaaagcag cug                                          23

<210> SEQ ID NO 3
<211> LENGTH: 22
<212> TYPE: RNA
<213> ORGANISM: Homo sapiens
<220> FEATURE:
<221> NAME/KEY: miRNA
<222> LOCATION: (1)..(22)

<400> SEQUENCE: 3
aaacaaacau ggugcacuuc uu                                           22

<210> SEQ ID NO 4
<211> LENGTH: 22
<212> TYPE: RNA
<213> ORGANISM: Homo sapiens
<220> FEATURE:
<221> NAME/KEY: miRNA
<222> LOCATION: (1)..(22)

<400> SEQUENCE: 4
aaaagcuggg uugagagggc ga                                           22

<210> SEQ ID NO 5
<211> LENGTH: 23
<212> TYPE: RNA
<213> ORGANISM: Homo sapiens
<220> FEATURE:
<221> NAME/KEY: miRNA
<222> LOCATION: (1)..(23)

<400> SEQUENCE: 5
uacccuguag auccgaauuu gug                                          23

<210> SEQ ID NO 6
<211> LENGTH: 21
<212> TYPE: RNA
<213> ORGANISM: Homo sapiens
<220> FEATURE:
<221> NAME/KEY: miRNA
<222> LOCATION: (1)..(21)

<400> SEQUENCE: 6

```
cauuauuacu uuugguacgc g                                         21

<210> SEQ ID NO 7
<211> LENGTH: 23
<212> TYPE: RNA
<213> ORGANISM: Homo sapiens
<220> FEATURE:
<221> NAME/KEY: miRNA
<222> LOCATION: (1)..(23)

<400> SEQUENCE: 7
uguaaacauc cuacacucuc agc                                       23

<210> SEQ ID NO 8
<211> LENGTH: 23
<212> TYPE: RNA
<213> ORGANISM: Homo sapiens
<220> FEATURE:
<221> NAME/KEY: miRNA
<222> LOCATION: (1)..(23)

<400> SEQUENCE: 8
aacauucaac gcugucggug agu                                       23

<210> SEQ ID NO 9
<211> LENGTH: 22
<212> TYPE: RNA
<213> ORGANISM: Homo sapiens
<220> FEATURE:
<221> NAME/KEY: miRNA
<222> LOCATION: (1)..(22)

<400> SEQUENCE: 9
uagcuuauca gacugauguu ga                                        22

<210> SEQ ID NO 10
<211> LENGTH: 22
<212> TYPE: RNA
<213> ORGANISM: Homo sapiens
<220> FEATURE:
<221> NAME/KEY: miRNA
<222> LOCATION: (1)..(22)

<400> SEQUENCE: 10
uguaaacauc cccgacugga ag                                        22

<210> SEQ ID NO 11
<211> LENGTH: 22
<212> TYPE: RNA
<213> ORGANISM: Homo sapiens
<220> FEATURE:
<221> NAME/KEY: miRNA
<222> LOCATION: (1)..(22)

<400> SEQUENCE: 11
uagcaccauc ugaaacggu ua                                         22

<210> SEQ ID NO 12
<211> LENGTH: 22
<212> TYPE: RNA
<213> ORGANISM: Homo sapiens
<220> FEATURE:
<221> NAME/KEY: miRNA
<222> LOCATION: (1)..(22)

<400> SEQUENCE: 12
ucccugagac ccuaacuugu ga                                        22
```

```
<210> SEQ ID NO 13
<211> LENGTH: 18
<212> TYPE: RNA
<213> ORGANISM: Homo sapiens
<220> FEATURE:
<221> NAME/KEY: miRNA
<222> LOCATION: (1)..(18)

<400> SEQUENCE: 13
uucacaggga ggugucau                                                   18

<210> SEQ ID NO 14
<211> LENGTH: 23
<212> TYPE: RNA
<213> ORGANISM: Homo sapiens
<220> FEATURE:
<221> NAME/KEY: miRNA
<222> LOCATION: (1)..(23)

<400> SEQUENCE: 14
agcagcauug uacagggcua uca                                             23

<210> SEQ ID NO 15
<211> LENGTH: 22
<212> TYPE: RNA
<213> ORGANISM: Homo sapiens
<220> FEATURE:
<221> NAME/KEY: miRNA
<222> LOCATION: (1)..(22)

<400> SEQUENCE: 15
agggcuuagc ugcuugugag ca                                              22

<210> SEQ ID NO 16
<211> LENGTH: 22
<212> TYPE: RNA
<213> ORGANISM: Homo sapiens
<220> FEATURE:
<221> NAME/KEY: miRNA
<222> LOCATION: (1)..(22)

<400> SEQUENCE: 16
uggcagugua uuguuagcug gu                                              22

<210> SEQ ID NO 17
<211> LENGTH: 23
<212> TYPE: RNA
<213> ORGANISM: Mus musculus
<220> FEATURE:
<221> NAME/KEY: miRNA
<222> LOCATION: (1)..(23)

<400> SEQUENCE: 17
ggcagaggag ggcuguucuu ccc                                             23

<210> SEQ ID NO 18
<211> LENGTH: 22
<212> TYPE: RNA
<213> ORGANISM: Homo sapiens
<220> FEATURE:
<221> NAME/KEY: miRNA
<222> LOCATION: (1)..(22)

<400> SEQUENCE: 18
ugccuacuga gcugauauca gu                                              22

<210> SEQ ID NO 19
```

```
<211> LENGTH: 22
<212> TYPE: RNA
<213> ORGANISM: Homo sapiens
<220> FEATURE:
<221> NAME/KEY: miRNA
<222> LOCATION: (1)..(22)

<400> SEQUENCE: 19
accuggcaua caauguagau uu                                              22

<210> SEQ ID NO 20
<211> LENGTH: 18
<212> TYPE: RNA
<213> ORGANISM: Homo sapiens
<220> FEATURE:
<221> NAME/KEY: miRNA
<222> LOCATION: (1)..(18)

<400> SEQUENCE: 20
ugcuuccuuu cagagggu                                                   18

<210> SEQ ID NO 21
<211> LENGTH: 23
<212> TYPE: RNA
<213> ORGANISM: Mus musculus
<220> FEATURE:
<221> NAME/KEY: miRNA
<222> LOCATION: (1)..(23)

<400> SEQUENCE: 21
uggaagacuu gugauuuugu ugu                                             23

<210> SEQ ID NO 22
<211> LENGTH: 22
<212> TYPE: RNA
<213> ORGANISM: Homo sapiens
<220> FEATURE:
<221> NAME/KEY: miRNA
<222> LOCATION: (1)..(22)

<400> SEQUENCE: 22
uucaccaccu ucuccaccca gc                                              22

<210> SEQ ID NO 23
<211> LENGTH: 23
<212> TYPE: RNA
<213> ORGANISM: Homo sapiens
<220> FEATURE:
<221> NAME/KEY: miRNA
<222> LOCATION: (1)..(23)

<400> SEQUENCE: 23
aguuuugcag guuugcaucc agc                                             23

<210> SEQ ID NO 24
<211> LENGTH: 23
<212> TYPE: RNA
<213> ORGANISM: Mus musculus
<220> FEATURE:
<221> NAME/KEY: miRNA
<222> LOCATION: (1)..(23)

<400> SEQUENCE: 24
ugucugcccg agugccugcc ucu                                             23

<210> SEQ ID NO 25
<211> LENGTH: 23
<212> TYPE: RNA
```

```
<213> ORGANISM: Homo sapiens
<220> FEATURE:
<221> NAME/KEY: miRNA
<222> LOCATION: (1)..(23)

<400> SEQUENCE: 25
uacccuguag aaccgaauuu gug                                           23

<210> SEQ ID NO 26
<211> LENGTH: 22
<212> TYPE: RNA
<213> ORGANISM: Rattus norvegicus
<220> FEATURE:
<221> NAME/KEY: miRNA
<222> LOCATION: (1)..(22)

<400> SEQUENCE: 26
ugagguagua gauuguauag uu                                            22

<210> SEQ ID NO 27
<211> LENGTH: 74
<212> TYPE: DNA
<213> ORGANISM: Unknown
<220> FEATURE:
<223> OTHER INFORMATION: mir-21 consensus sequence

<400> SEQUENCE: 27
tgtaccacct tgtcgggtag cttatcagac tgatgttgac tgttgaatct catggcaaca   60
gcagtcgatg ggct                                                     74

<210> SEQ ID NO 28
<211> LENGTH: 74
<212> TYPE: DNA
<213> ORGANISM: Rattus norvegicus

<400> SEQUENCE: 28
tgtaccacct tgtcgggtag cttatcagac tgatgttgac tgttgaatct catggcaaca   60
gcagtcgatg ggct                                                     74

<210> SEQ ID NO 29
<211> LENGTH: 74
<212> TYPE: DNA
<213> ORGANISM: Mus musculus

<400> SEQUENCE: 29
tgtaccacct tgtcggatag cttatcagac tgatgttgac tgttgaatct catggcaaca   60
gcagtcgatg ggct                                                     74

<210> SEQ ID NO 30
<211> LENGTH: 64
<212> TYPE: DNA
<213> ORGANISM: Homo sapiens

<400> SEQUENCE: 30
tgtcgggtag cttatcagac tgatgttgac tgttgaatct catggcaaca ccagtcgatg   60
ggct                                                                64

<210> SEQ ID NO 31
<211> LENGTH: 74
<212> TYPE: DNA
<213> ORGANISM: Cricetulus griseus

<400> SEQUENCE: 31
```

-continued

```
tgtaccacct tgtcgggtag cttatcagac tgatgttgac tgttgaatct catggcaaca     60
gcagtcgatg ggct                                                       74

<210> SEQ ID NO 32
<211> LENGTH: 64
<212> TYPE: DNA
<213> ORGANISM: Bos taurus

<400> SEQUENCE: 32
tgtcgggtag cttatcagac tgatgttgac tgttgaatct catggcaaca gcagtcgatg     60
ggct                                                                  64

<210> SEQ ID NO 33
<211> LENGTH: 42
<212> TYPE: RNA
<213> ORGANISM: Cricetulus griseus

<400> SEQUENCE: 33
uguaccaccu ugucggguag cuuaucagac ugauguugac ug                        42

<210> SEQ ID NO 34
<211> LENGTH: 40
<212> TYPE: RNA
<213> ORGANISM: Cricetulus griseus

<400> SEQUENCE: 34
uggcaacagc agucgauggg cugucugaca uuuugguauc                           40
```